US012521254B2

(12) United States Patent
Firmbach et al.

(10) Patent No.: US 12,521,254 B2
(45) Date of Patent: Jan. 13, 2026

(54) SURGICAL INSTRUMENT SYSTEM

(71) Applicant: Aesculap AG, Tuttlingen (DE)

(72) Inventors: Franz-Peter Firmbach, Emmingen-Liptingen (DE); Svenja Anhorn, Heroldstatt (DE)

(73) Assignee: Aesculap AG, Tuttlingen (DE)

( * ) Notice: Subject to any disclaimer, the term of this patent is extended or adjusted under 35 U.S.C. 154(b) by 259 days.

(21) Appl. No.: 18/321,860

(22) Filed: May 23, 2023

(65) Prior Publication Data

US 2023/0380989 A1 Nov. 30, 2023

(30) Foreign Application Priority Data

May 24, 2022 (DE) ..................... 10 2022 205 192.0

(51) Int. Cl.
*A61B 17/15* (2006.01)
*A61F 2/46* (2006.01)

(52) U.S. Cl.
CPC ............ *A61F 2/461* (2013.01); *A61B 17/155* (2013.01)

(58) Field of Classification Search
CPC ... A61B 17/155; A61B 2017/564; A61F 2/38; A61F 2/461; A61F 2/4657; A61F 2002/4661
See application file for complete search history.

(56) References Cited

U.S. PATENT DOCUMENTS 5,662,656 A 9/1997 White
5,676,668 A 10/1997 Mccue et al.
5,683,397 A 11/1997 Vendrely et al.
10,130,375 B2 11/2018 Yager et al.
2004/0153084 A1 8/2004 Haney et al.
2011/0060340 A1 3/2011 Dees, Jr. et al.
2016/0030053 A1 2/2016 Yager et al.
2017/0258599 A1* 9/2017 Richter ................. A61F 2/3886
2017/0348009 A1 12/2017 Dmuschewsky
(Continued)

FOREIGN PATENT DOCUMENTS

DE 69722052 T2 4/2004
DE 69636636 T2 8/2007
DE 102015100049 A1 7/2016
(Continued)

*Primary Examiner* — Samuel S Hanna

(74) *Attorney, Agent, or Firm* — Christopher A. Rothe; CM Law

(57) ABSTRACT

A surgical instrument system for use in a total knee arthroplasty includes a reference block that is attachable to a femur. The reference block has a block front side and a block rear side lying opposite the block front side. At least one compensation element has an element rear side and, lying opposite along the proximal-distal axis, a contact face for contacting a lateral condyle and/or medial condyle. A connection system has at least one connection portion on the reference block. At least one complementary connection portion is disposed on the compensation element. The connection system is configured to releasably attach the compensation element on the block front side. The compensation element in the attached state does not completely cover the block front side. The connection system is configured so that the compensation element is attachable in different positions on the block front side by the connection system.

3 Claims, 9 Drawing Sheets

(56) References Cited

U.S. PATENT DOCUMENTS

2021/0236143 A1 8/2021 Shah

FOREIGN PATENT DOCUMENTS

| | | | |
|---|---|---|---|
| WO | 9514444 | A1 | 6/1995 |
| WO | 9721390 | A1 | 6/1997 |
| WO | 9920192 | A1 | 4/1999 |
| WO | 2018216026 | A1 | 11/2018 |

* cited by examiner

SURGICAL INSTRUMENT SYSTEM

CROSS-REFERENCE TO RELATED APPLICATIONS

This application claims priority under 35 U.S.C. § 119 to German Application No. 10 2022 205 192.0, filed May 24, 2022, the content of which is incorporated by reference herein in its entirety.

FIELD

The present disclosure relates to a surgical instrument system for use in a total knee arthroplasty, having a reference block which is specified to be attached to a distal femur and has a block front side and, lying opposite along a proximal-distal axis, a block rear side; at least one compensation element which has an element rear side and, lying opposite along the proximal-distal axis, a contact face that is specified to contact a lateral condyle and/or a medial condyle of the distal femur; and having a connection system which has at least one connection portion that is disposed on the reference block, and at least one complementary connection portion that is disposed on the compensation element, and which connection system is specified to releasably attach the compensation element on the block front side.

BACKGROUND

A surgical instrument system is known from U.S. Pat. No. 10,130,375 B2 and is provided for use in a total knee arthroplasty (abbreviated as TKA). The known surgical instrument system has a reference block and at least one compensation element referred to as a shim. The reference block is specified to be attached to a distal femur and has a block front side and a block rear side that lies opposite the latter. When used, the block front side faces the distal condyles of the femur. The compensation element has an element rear side and a contact face that lies opposite the latter. The contact face is specified to contact one of the distal femoral condyles. In the known surgical instrument system, the contact face is congruent with the block front side such that the latter in the attached state of the compensation element is completely covered. For releasable attachment of the compensation element, the reference block has a type of plug receptacle. The compensation element on the rear side is provided with a protrusion which is releasably insertable into the plug receptacle. The plug receptacle and the protrusion form a type of connection system.

SUMMARY

It is an object of the present disclosure to provide a surgical instrument system of the type mentioned at the outset which makes possible the particularly versatile use of the latter in a manner adapted to the respective patient while simultaneously permitting a simple construction and enabling improved surgical results.

This object is achieved in that the at least one compensation element in the attached state does not completely cover the block front side at least in terms of an anterior-posterior axis of the reference block, and in that the connection system is specified in such a manner that the compensation element by means of the connection system is able to be attached in different positions on the block front side at least in terms of the anterior-posterior axis. The solution according to the present disclosure enables the compensation element to be positioned in an adapted manner with a view to a position and/or local characteristic of condylar bone and/or cartilage wear to be compensated by means of the compensation element. The different positioning of the compensation element on the reference block depends on the size of the defect to be compensated and/or whether the defect to be compensated in terms of the anterior-posterior axis is located in the upper, centric or lower region on the medial and/or lateral condyle of the distal femur. For this purpose, the connection system is specified according to the present disclosure in such a manner that the compensation element is attachable in different positions along the anterior-posterior axis on the block front side. Since the compensation element in the attached state does not completely cover the block front side at least in terms of the anterior-posterior axis, an ideally unrestricted view of the surgeon onto the contact point between the contact face and the respective condyle is simultaneously made possible independently of the respective assumed position of the compensation element. As a result of the solution according to the present disclosure, the surgical instrument system can be used in a flexible manner and is adaptable to the geometry and the location of the condylar wear to be compensated. Combined with the simultaneously improved or in any case not compromised visibility of the contact point, improved surgical results are made possible.

The reference block is preferably specified for the intramedullary attachment to the distal femur. For this purpose, the reference block preferably has a passage which extends between the block front side and the block rear side and is specified to receive an intramedullary rod. Such an intramedullary attachment is in principle known to the person skilled in the art and therefore does not require further explanation. Alternatively or additionally, the reference block may be specified for an extramedullary attachment. This is likewise performed in a way known in principle to the person skilled in the art. In the use of the surgical instrument system, the block front side faces the distal femur and is proximally oriented. The opposite block rear side is distally oriented. The block rear side is preferably specified for the releasable attachment of a femoral cut guide. In the attached state, and upon performed compensation of the condylar wear by means of the at least one compensation element, the reference block can serve as a reference for saw cuts to be carried out on the distal femur while using the femoral cut guide. The reference block preferably has the proximal-distal axis, the anterior-posterior axis, and a medial-lateral axis, which are mutually orthogonal and thus form a Cartesian reference axis system. For the sake of completeness, it is to be noted that said axes of the reference block preferably correspond to the corresponding body axes of the patient when the surgical instrument system is used. In other words, the anterior-posterior axis can also be referred to as the vertical axis, the medial-lateral axis can also be referred to as the transverse axis, and the proximal-distal axis can also be referred to as the longitudinal axis of the reference block. In embodiments of the present disclosure, the reference block has an integral or monobloc design. In other embodiments, the reference block has a multi-parts design.

The at least one compensation element by way of its element rear side faces the block front side when the surgical instrument system is in use. The opposite contact face faces the distal femur. In the attached state of the compensation element, a proximal-distal axis of the compensation element is preferably aligned parallel to the proximal-distal axis of the reference block. In the attached state, the compensation element does not completely cover and/or does incompletely cover the block front side. Said coverage or overlap is not complete at least in terms of the anterior-posterior axis, thus in the vertical direction of the reference block. Preferably, the overlap is additionally incomplete in terms of the medial-lateral axis of the reference block, i.e. in the transverse direction of the reference block. In other words, the compensation element is not as high and optionally additionally not as wide as the block front side. As a result, the compensation element can be positioned in the different positions on the block front side without a circumferential contour of the compensation element protruding beyond a circumferential contour of the block front side. This promotes said improved visibility of the contact point. The at least one compensation element has a defined thickness along the proximal-distal axis. The surgical instrument system preferably has a plurality of different compensation elements with different defined thicknesses, which are specified to compensate condylar bone and/or cartilage wear of different intensity. In embodiments of the present disclosure, the at least one compensation element has an integral or monobloc design. In other embodiments, the compensation element has a multi-parts design.

The connection system in portions is disposed and/or formed on the reference block and in portions disposed and/or formed on the at least one compensation element. Accordingly, the connection system has the at least one connection portion disposed and/or formed on the reference block and the at least one complementary connection portion disposed and/or formed on the compensation element. If the surgical instrument system has a plurality of compensation elements, each of the compensation elements has at least one complementary connection portion, wherein all of the complementary connection portions are to be associated with the connection system. For releasably attaching the compensation element to the reference block, the at least one connection portion and the at least one complementary connection portion interact in a form-fitting and/or force-fitting manner. The releasable connection between the connection portion and the complementary connection portion in different embodiments is, for example, a plug connection, clamping connection, latching connection, tongue-and-groove connection, guide slot connection, or the like. A magnetic connection is also conceivable in principle. In order to enable the positioning of the compensation element in the different positions, in embodiments of the present disclosure a plurality of connection portions are disposed and/or configured so as to be mutually spaced apart on the reference block, for example. In other embodiments, only one connection portion is present on the reference block, for example, said one connection portion in a state connected to the complementary connection portion permitting at least one degree of freedom of the compensation element in relation to the reference block. For example, a rotating, pivoting and/or linear movement of the compensation element in relation to the reference block can be provided for the different positioning. As a result, the compensation element in a state already attached to the block front side can be rotated, pivoted and/or pushed to different positions.

In one embodiment, the at least one connection portion is disposed on the block front side, and the at least one complementary connection portion is disposed on the element rear side. Such an arrangement can offer advantages in terms of manufacturing and/or ergonomics when attaching the compensation element. However, such an arrangement is not mandatory. In other embodiments, the complementary connection portion is disposed on a circumferential contour, i.e. laterally, on the upper and/or the lower side, on the compensation element. The same can apply, mutatis mutandis, for the disposal of the at least one connection portion on the reference block, wherein a disposal on the block rear side of the latter is also conceivable.

In one embodiment, the at least one connection portion is a female connection portion recessed in the reference block, and the at least one complementary connection portion is a male connection portion protruding from the compensation element. Such a design can offer advantages in terms of manufacturing and/or ergonomics in use, especially when attaching the compensation element. The at least one connection portion is preferably recessed in the block front side. The at least one complementary connection portion preferably protrudes from the element rear side. A recessed, i.e. female, design can in particular be embodied as a bore, depression, concavity, groove, slot, or the like. A protruding, i.e. male, design can in particular be embodied as a pin, stud, bolt, strip, hook, or the like. In further embodiments, a reversed assignment of male and female portions is provided.

In one embodiment, the block front side has a medial portion and a lateral portion that is spaced apart along a medial-lateral axis of the reference block, which portions have in each case at least one connection portion of the connection system, wherein the at least one compensation element for contacting the lateral condyle is able to be attached on the lateral portion, and for contacting the medial condyle is able to be attached on the medial portion. As a result, an even more versatile and particularly adaptable use is made possible. This is because the at least one compensation element in this embodiment of the present disclosure is selectively specified to compensate wear of the lateral condyle or of the medial condyle. To this end, the compensation element can selectively be attached either on the lateral portion or the medial portion. For this purpose, the connection system on both portions of the block front side has at least one connection portion. Accordingly, these connection portions can also be referred to as a lateral connection portion or a medial connection portion, respectively. The compensation element in turn can be positioned differently at least in terms of the anterior-posterior axis on the medial portion as well as on the lateral portion.

In one embodiment, the connection system has a plurality of connection portions which are disposed on the reference block so as to be spaced apart along the anterior-posterior axis, wherein the at least one complementary connection portion for the different positioning of the compensation element is selectively connectable to one of the connection portions disposed at a spacing. The connection portions disposed at a spacing define, so to speak, a plurality of different connection points, interfaces, attachment points or the like, where the at least one compensation element can be attached. If the block front side has a medial portion and a lateral portion, the plurality of connection portions disposed at a spacing can be disposed only on one of the two portions or on both portions. In embodiments, a plurality of connection portions disposed at a spacing along the medial-lateral axis are moreover disposed and/or formed on the medial portion. As a result, the at least one compensation element can be attached on the block front side so as to be differently offset in the medial-lateral direction. Accordingly, a plurality of connection portions disposed at a spacing along the medial-lateral axes can alternatively or additionally be disposed and/or formed on the lateral portion of the block front side.

In one embodiment, the connection portions disposed at a spacing comprise in each case at least one bore incorporated in the block front side, and the at least one complementary connection portion comprises at least one pin which is disposed on the element rear side and in the attached state of the compensation element is inserted axially into the at least one bore. This embodiment is particularly easy to manufacture. Moreover, the resulting construction is particularly robust. The bores define in each case at least one plug-in point for inserting the pin and thus for attaching the compensation element. In the inserted state, the pin is held in a form-fitting manner in the bore along the anterior-posterior axis and along the medial-lateral axis. The pin is able to be inserted into the bore and extracted from the latter in a sliding manner along the proximal-distal axis. Depending on the specific shaping of the bore and/or of the pin, the pin can engage in the bore so as to be rotatable relative to the latter about the pin longitudinal axis, or so as to co-rotate with the bore. Each of the plurality of connection portions disposed at a spacing comprises at least one bore. In design embodiments, the plurality of connection portions disposed at a spacing comprise in each case a plurality of bores. In the latter case, the complementary connection portion of the compensation element comprises a corresponding number of pins.

In one embodiment, the connection portions disposed at a spacing are in each case designed as a bore pair, and the at least one complementary connection portion is designed as a pin pair. The bores of the bore pairs are in each case preferably embodied with a circular-cylindrical cross section. The same preferably applies, mutatis mutandis, to the pins of the pin pairs. This again offers advantages in terms of manufacturing. Nevertheless, owing to the design as a bore pair and a pin pair, a rotatably fixed attachment of the at least one compensation element in the plane of the block front side can be achieved in a simple manner. The two bores of the respective bore pairs are mutually spaced apart in the plane of the block front side and thus along the anterior-posterior axis and/or the medial-lateral axis. The same applies, mutatis mutandis, to the two pins.

In one embodiment, the connection portions disposed at a spacing are in each case designed as an undercut groove, and the at least one complementary connection portion is designed as a strip which in the attached state of the compensation element is pushed in the longitudinal direction of the groove into the latter. The undercut grooves are in each case incorporated in the block front side so as to be elongate in the anterior-posterior direction and/or the medial-lateral direction. In order for the compensation element to be attached, the strip can be pushed in the longitudinal direction of the groove into the latter. Accordingly, in the use of the surgical instrument system, the compensation element is pushed from the outside laterally, from above or from below, onto the block front side of the reference block already attached to the distal femur. This can offer ergonomic advantages. The grooves are in each case undercut. The complementary strip has a design that corresponds to the undercut. As a result, the strip and thus the compensation element in a state pushed into the groove are held in the groove in a form-fitting manner perpendicularly to the longitudinal extent of the groove. Consequently, the compensation element cannot be simply lifted from the block front side in the normal direction, but for the purpose of disassembly must be pulled off the reference block from the block front side along the groove. The undercut grooves form in each case a connection point for attaching the compensation element in different positions. The undercut grooves are disposed on the block front side so as to be mutually spaced apart along the anterior-posterior axis. Additionally, the undercut grooves can be disposed on the block front side so as to be mutually spaced apart along the medial-lateral axis. If the block front side has a medial portion and a lateral portion, each of the two portions can have a plurality of undercut grooves which are disposed at a spacing along the anterior-posterior axis and/or the medial-lateral axis.

In one embodiment, the at least one connection portion is a guide slot which is incorporated in the block front side and elongate along the anterior-posterior axis and in which the complementary connection portion for the different positioning of the compensation element engages in a form-fitting manner perpendicularly to the longitudinal direction so as to be displaceable in the longitudinal direction of the guide slot. Accordingly, in this embodiment of the present disclosure, there are not a plurality of connection portions, which are disposed so as to be mutually spaced apart along the anterior-posterior axis, disposed on the block front side. Instead, the at least one connection portion extends along the anterior-posterior axis. For the different positioning of the compensation element, the complementary connection portion can be displaced along the guide slot and accordingly be attached on the block front side at different positions at least in terms of the vertical direction of the reference block. When interacting with the guide slot, the complementary connection portion functions as a guide element which can be designed in the form of, for example, a guide pin, guide bolt, guide stud, or in another suitable way. If the block front side has a medial portion and a lateral portion, each of the two portions is in each case preferably provided with at least one guide slot.

In one embodiment, the guide slot in portions is elongate in the medial-lateral direction. As a result, the compensation element by means of displacing the complementary connection portion along the guide slot can be positioned differently not only in terms of the anterior-posterior axis but additionally also in terms of the medial-lateral axis. As a result, an even more improved adaptability to the condylar defect to be compensated is achieved.

In one embodiment, the guide slot in the longitudinal direction is open at one end and has an introduction opening for introducing the complementary connection portion which is disposed on a circumferential contour of the reference block. Accordingly, the introduction opening can be disposed on an upper side, a lower side, a medial or a lateral side of the reference block. For attaching the compensation element, the complementary connection portion can be pushed into the introduction opening in the plane of the block front side. This offers ergonomic advantages in the use of the surgical instrument system.

In one embodiment, the at least one connection portion is a cylindrical bore incorporated in the block front side, and the at least one complementary connection portion is a cylindrical pin which is disposed eccentrically on the element rear side and in the attached state of the compensation element is inserted axially into the bore, wherein the compensation element, owing to the eccentric disposal of the pin, by means of a rotation about the longitudinal axis of the latter is able to be positioned differently at least in terms of the anterior-posterior axis. For the different positioning, the compensation element can be rotatably positioned in different orientations in terms of the proximal-distal axis. For this purpose, the bore is cylindrically embodied, on the one hand. Moreover, the pin is cylindrically embodied and disposed eccentrically on the element rear side. As a result of the eccentric disposal of the pin, a rotation about the longitudinal axis of the pin causes not only a different orientation but additionally a displacement of the compensation element relative to the reference block. This displacement is performed along the anterior-posterior axis and/or the medial-lateral axis. In the simplest case, the block front side has only a single cylindrical bore for receiving the cylindrical and eccentrically disposed pin. If the block front side has a medial portion and a lateral portion, each of the two portions is preferably provided with a cylindrical bore. This embodiment of the present disclosure offers advantages in terms of manufacturing because only one connection portion in the form of the cylindrical bore has to be incorporated in the block front side.

In one embodiment, the compensation element and/or the contact face has a circular circumferential contour. The inventors have recognized that the circular circumferential contour in combination with the eccentric disposal of the cylindrical pin on the element rear side offers particular advantages.

BRIEF DESCRIPTION OF THE DRAWINGS

Further advantages and features of the present disclosure follow from the description of preferred exemplary embodiments of the present disclosure which are illustrated by means of the drawings in which.

DETAILED DESCRIPTION

Figure 1:
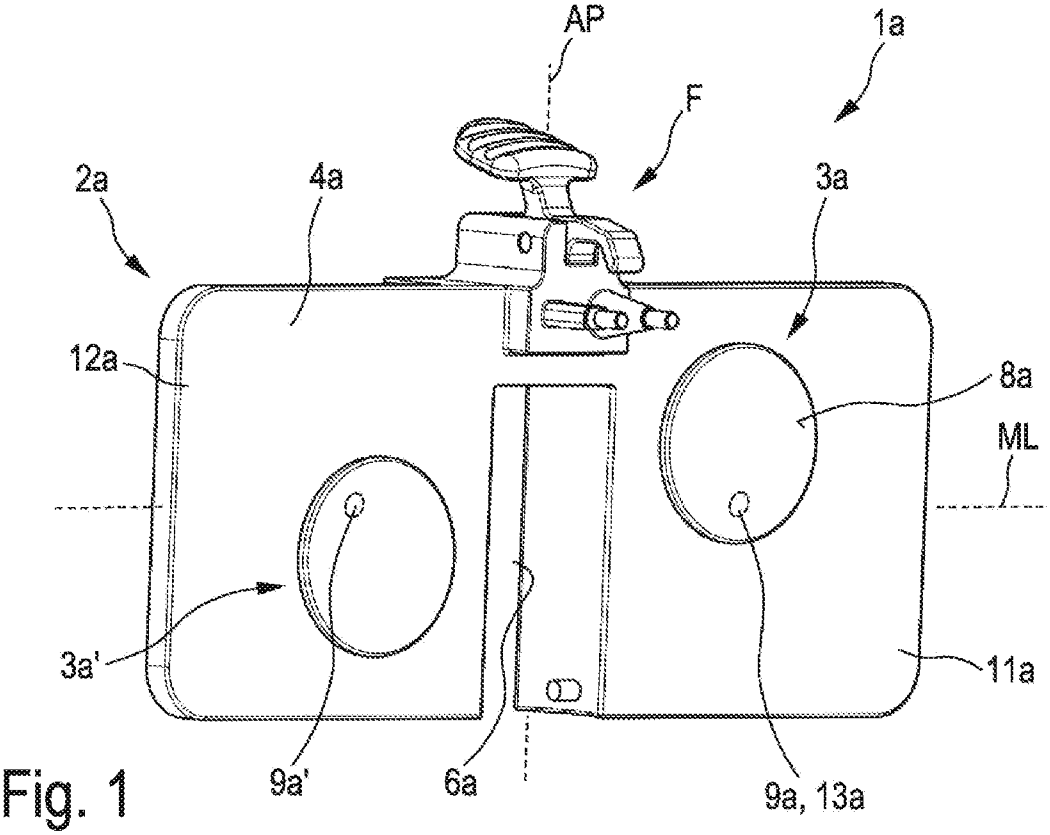
FIG. 1 shows in a schematic perspective view an embodiment of a surgical instrument system according to the present disclosure, having a reference block and at least one compensation element, viewed in the direction of a block front side of the reference block.

According to FIG. 1, a surgical instrument system 1*a* is provided for use in a total knee arthroplasty. Specifically, the surgical instrument system 1*a* serves for positioning and/or aligning a femoral cutting guide, also known as cutting jig, for carrying out saw cuts on a distal femur. In this context, the surgical instrument system 1*a* allows compensation of condylar bone and/or cartilage defects. The surgical instrument system 1*a* may also be referred to as an alignment system.

The surgical instrument system 1*a* has a reference block 2*a* and at least one compensation element 3*a*.

Figure 4:
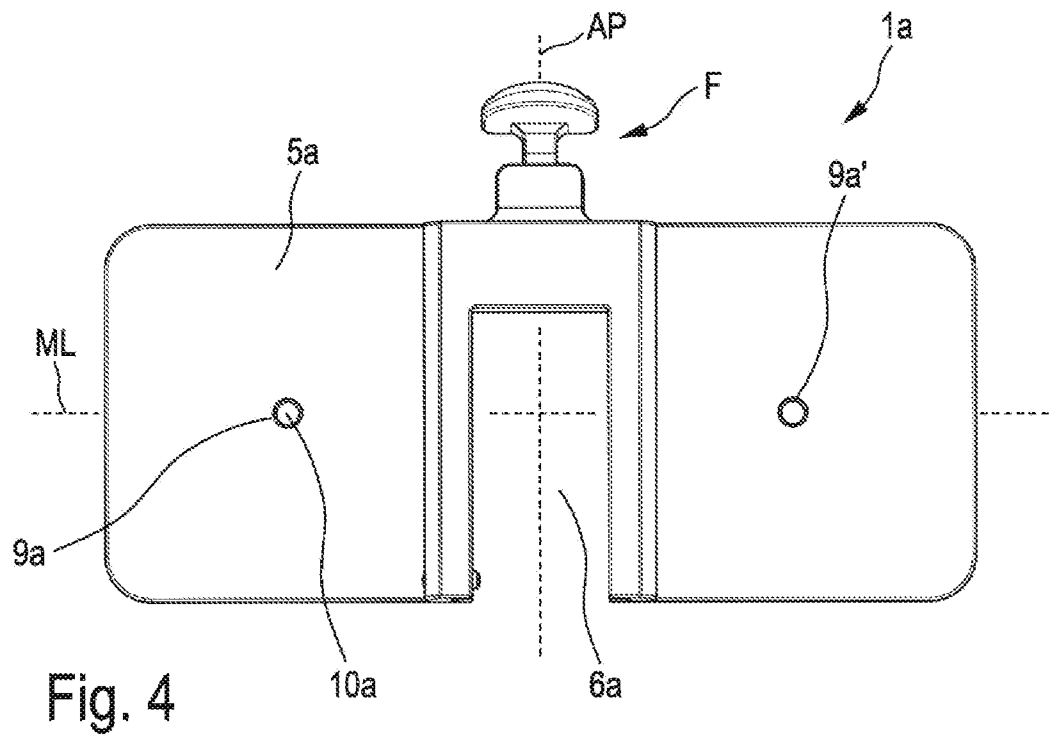
FIG. 4 shows a schematic rear view of the surgical instrument system according to FIG. 1.
Figure 5:
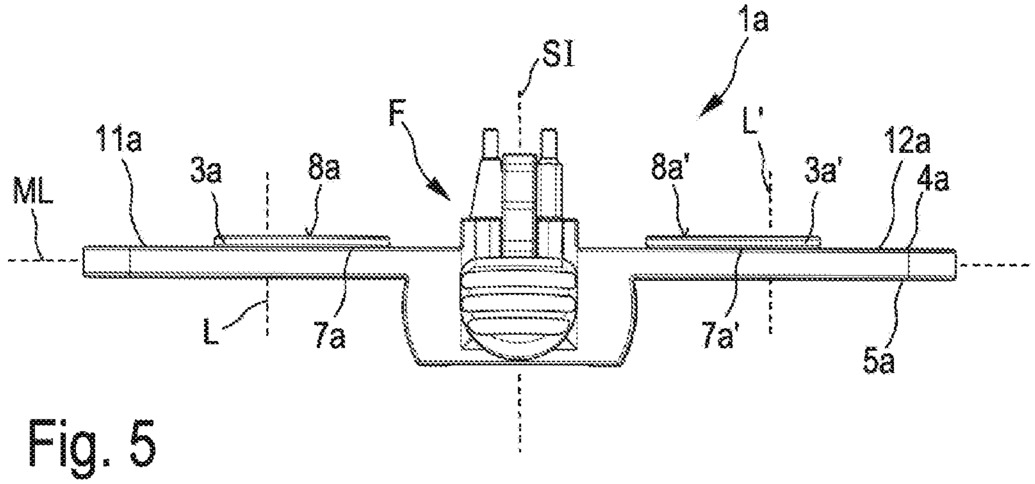
FIG. 5 shows a schematic plan view of the surgical instrument system according to FIGS. 1 and 4.
Figure 6:
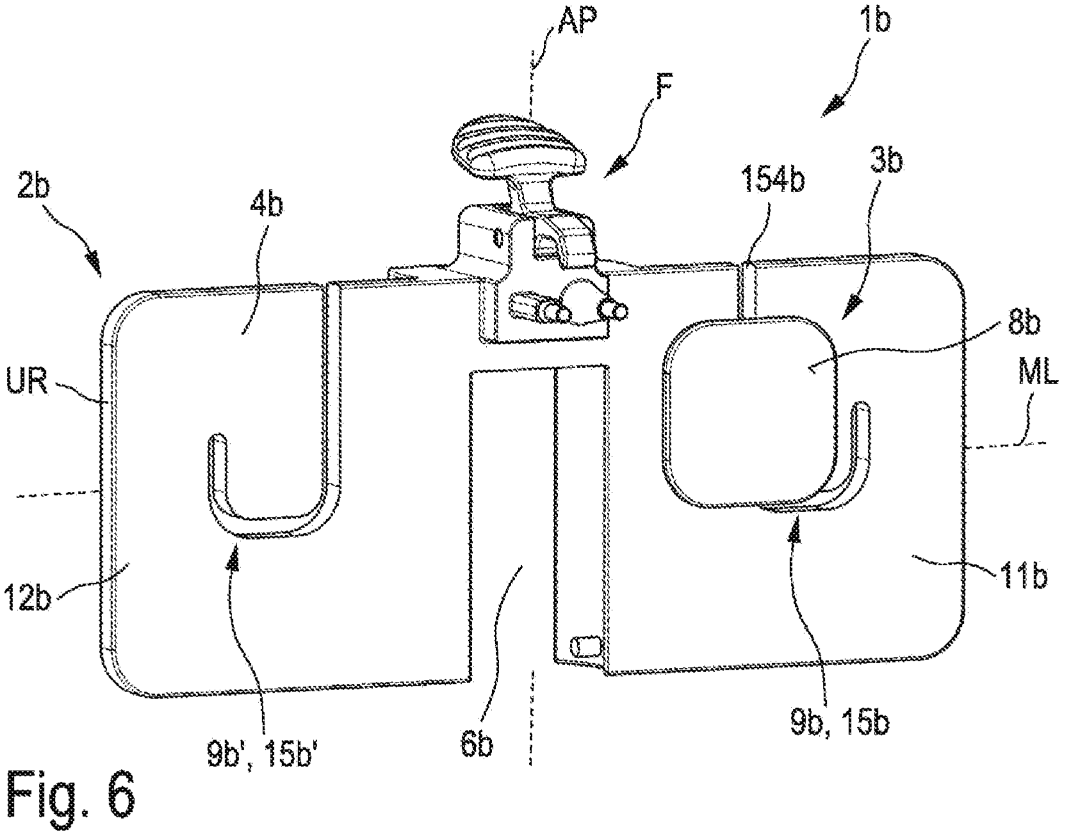
FIG. 6 shows in a schematic perspective view a further embodiment of a surgical instrument system according to the present disclosure.
Figure 7:
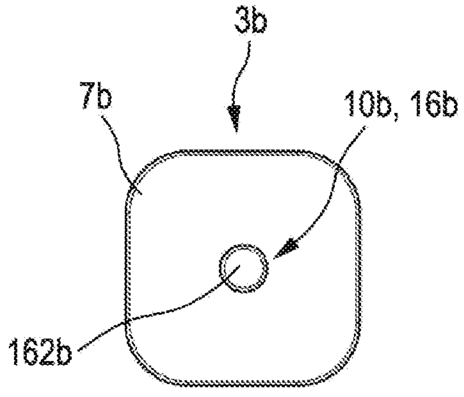
FIG. 7 shows a schematic rear view of a compensation element of the surgical instrument system according to FIG. 6.
Figure 8:
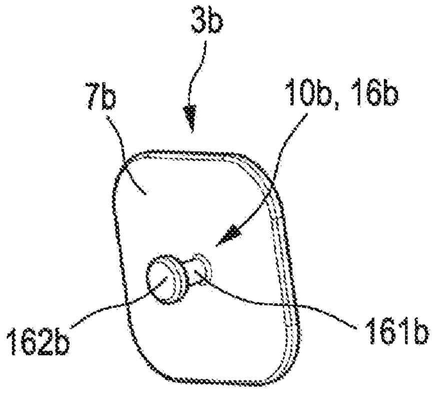
FIG. 8 shows a perspective rear view of the compensation element of the surgical instrument system according to FIG. 6.

The reference block 2*a* is specified to be attached to a distal femur of a patient (not shown in more detail) and has a block front side 4*a* and, lying opposite along a proximal-distal axis SI (FIG. 5), a block rear side 5*a* (FIG. 4). In the use of the surgical instrument system 1*a*, the block front side 4*a* faces the distal femur, more specifically the condyles thereof. The block rear side 5*a* faces away from the distal femur.

Attaching the reference block 2*a* on the distal femur is performed in a way known in principle to the person skilled in the art. For example, an intramedullary and/or extramedullary attachment can be provided. For the intramedullary attachment, the reference block 2*a* in the case of the embodiment shown has a passage 6*a* which extends continuously between the block front side 4*a* and the block rear side 5*a* and is specified to receive an intramedullary rod. Further details pertaining to the attachment are not essential for the present disclosure so that further explanations in this respect can be dispensed with.

The reference block 2*a* can also be referred to as an alignment plate. In the embodiment shown, the reference block 2*a* has a plate-shaped design having an approximately rectangular circumferential contour. Aside from said proximal-distal axis SI, the reference block 2*a* has an anterior-posterior axis AP and a medial-lateral axis ML. Said axes SI, AP, ML form a Cartesian axis system. Said axes SI, AP, ML in the actual use of the surgical instrument 1*a* preferably correspond to the respective anatomical body axis of the patient.

In terms of the dimensions of the reference block 2*a*, the anterior-posterior axis AP can also be referred to as the vertical axis and/or Z-axis of the reference block 2*a*. The medial-lateral axis ML can also be referred to as the transverse axis and/or Y-axis of the reference block 2*a*. The proximal-distal axis SI can also be referred to as the longitudinal axis and/or X-axis of the reference block 2*a*.

The block rear side 5*a* in a way not shown in more detail is specified to releasably attach the already mentioned femoral cutting guide. The block rear side 5*a* can be specified to receive additional or alternative components so that a use exclusively in combination with said femoral cutting guide is not mandatory.

Moreover, in the embodiment shown, the reference block 2*a* has a functional unit F which in terms of the medial-lateral axis ML is disposed so as to be approximately centric, and in terms of the anterior-posterior axis AP is disposed on the upper side. The functional unit F is provided for releasably coupling the reference block 2*a* to further components not identified in more detail. This aspect, however, is not essential for the present disclosure. Any further explanation pertaining to structural and/or functional features of the functional unit F can therefore be dispensed with.

The at least one compensation element 3*a* (see FIGS. 2, 3, in particular) has an element rear side 7*a* and an opposite contact face 8*a*. The contact face 8*a* is specified to contact the distal femur. The at least one compensation element 3*a* in a way yet to be described in more detail is specified to be releasably attached to the block front side 4*a*. In the attached state shown by means of FIG. 1, the contact face 8*a* is aligned parallel to the block front side 4*a* and faces away from the latter. In the use of the surgical instrument system 1*a*, the contact face 8*a* faces the distal femur and bears either on the lateral condyle or the medial condyle of the latter. The element rear side 7*a* in the attached state of the compensation element 3*a* is oriented parallel to the block front side 4*a* and faces the latter.

Provided for releasably attaching the compensation element 3*a* is a connection system which has at least one connection portion 9*a* disposed on the reference block 2*a*, and a complementary connection portion 10*a* disposed on the compensation element 3*a*. The connection system is specified in such a manner that the compensation element 3*a* by means of the connection system is able to be attached on the block front side 4*a* in different positions at least in terms of the anterior-posterior axis AP. The compensation element 3*a* in the attached state does not completely cover the block front side 4*a* at least in terms of the anterior-posterior axis AP. In other words, the compensation element 3*a*, in particular the contact face 8*a* thereof, is not as high as the block front side 4*a*. In the present case, the compensation element 3*a*, and thus also the contact face 8*a* thereof, in terms of the medial-lateral axis ML is also smaller than the block front side, i.e. not as wide in the transverse direction. Owing to the design of the connection system yet to be described in detail, the compensation element 3*a* can be positioned relative to the block front side 4*a* in a way adapted to the bone and/or cartilage defect to be compensated. Since the compensation element 3*a* in the way described above is smaller than the block front side 4*a*, an ideally unobstructed visibility of the contact point between the contact face 8*a* and the respective distal condyle is nevertheless guaranteed.

In the embodiment shown, the block front side 4*a* has a medial portion 11*a* and a lateral portion 12*a*. The medial portion 11*a* and the lateral portion 12*a* of the block front side 4*a* are separated from each other by the passage 6*a* and to this extent spaced apart from each other along the medial-lateral axis ML. The compensation element 3*a* in the state shown by means of FIG. 1 is attached on the medial portion 11*a*. For this purpose, the medial portion 11*a* has the connection portion 9*a*. For an alternative attachment of the compensation element 3*a* on the lateral portion 12*a*, the latter presently has a further connection portion 9*a*' of the connection system. Accordingly, the compensation element 3*a* can selectively be applied to the medial portion 11*a* or to the lateral portion 12*a*. This depending on whether a cartilage and/or a bone defect on the medial condyle or the lateral condyle has to be compensated.

Moreover, the surgical instrument system 1*a* preferably has a plurality of compensation elements which can primarily differ from one another in their thickness in terms of the proximal-distal axis. For example, different thicknesses of the different compensation elements of 1 mm, 2 mm, 3 mm, 4 mm, etc., are conceivable. The thickness of the compensation element to be used usually depends on a degree of the manifestation of the bone or cartilage defect, or a degree of wear on the condyle.

In the embodiment shown, the reference block 2*a* is specified in such a manner that the block front side 4*a* can function as a compensation face for a condyle which is unworn, or worn to a practically insignificant extent. This means that the attachment of a compensation element is not required in the absence of noticeable wear.

In FIG. 1, the surgical system 1*a* is shown in a state in which, additionally to the compensation element 3*a*, a further compensation element 3*a*' is attached on the block front side 4*a*. The further compensation element 3*a*' is presently attached on the lateral portion 12*a*. In the configuration shown, the further compensation element 3*a*' in terms of design is identical to the compensation element 3*a* so that further explanations pertaining thereto can be dispensed with. It is understood that instead of the further compensation element 3*a*' a compensation element with a different thickness may be used, for example.

The further explanations pertaining to the connection system and thus to the connection portion 9*a* and to the complementary connection portion 10*a* are provided with reference to the compensation element 3*a* and the medial portion 11*a* of the block front side. It is understood that the relevant explanations can readily be applied to the further compensation element 3*a*' and the lateral portion 12*a* having the further connection portion 9*a*' disposed thereon.

In the embodiment according to FIGS. 1 to 5, the connection portion 9*a* is a cylindrical bore 13*a*, and the complementary connection portion 10*a* is a cylindrical pin 14*a* which is disposed eccentrically on the element rear side 7*a*. As a result, the compensation element 3*a* in the attached state shown by means of FIG. 1, by means of a rotation about a longitudinal axis L (FIG. 3) of the cylindrical pin 14*a*, is able to be positioned on the reference block 2*a* in different positions relative to the block front side 4*a*. As a result of said rotation about the longitudinal axis L, the orientation of the compensation element 3*a* and thus—owing to the eccentric disposal of the cylindrical pin 14*a*—also the positioning in terms of the anterior-posterior axis changes. In the present case, the position in terms of the medial-lateral axis ML is also altered. For attaching the compensation element 3*a*, the cylindrical pin 14*a* is inserted along the longitudinal axis L thereof, which is oriented parallel to the proximal-distal axis SI, into the cylindrical bore 13*a*. In the inserted state, the cylindrical pin 14*a* in the radial direction is held in a form-fitting manner in the cylindrical bore 13*a*. To this extent, the cylindrical pin 14*a* is immobile in terms of the anterior-posterior axis AP and the medial-lateral axis ML. For the different positioning, the compensation element 3*a* is rotated about the longitudinal axis L, the cylindrical pin 14*a* in the circumferential direction sliding relative to the cylindrical bore 13*a* in the process. As a result, the contact face 8*a* can be positioned further upwards, downwards, inwards and/or outwards, adapted to the respective position of the condylar wear to be compensated.

Figure 2:
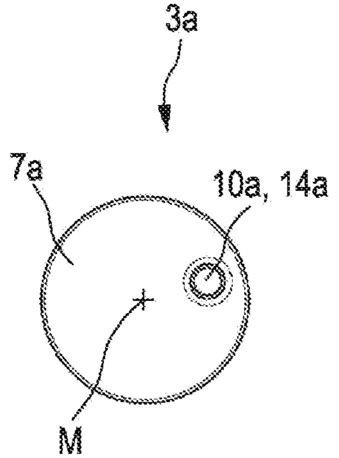
FIG. 2 shows in a schematic detailed view the at least one compensation element of the surgical instrument system according to FIG. 1, viewed in the direction of an element rear side.
Figure 3:
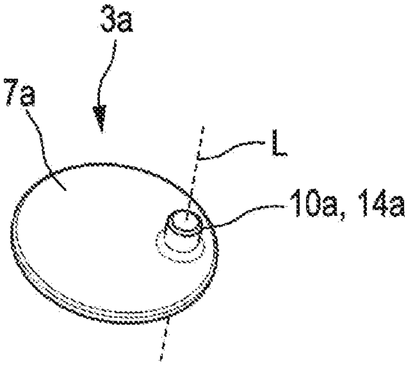
FIG. 3 shows a schematic perspective view of the compensation element according to FIG. 2.

In the embodiment shown, the compensation element 3*a* has a circular circumferential contour U (FIGS. 2, 3). The same applies, mutatis mutandis, to the contact face 8*a*. The circular circumferential contour U, in particular in the context of the present design of the connection system for rotatable positioning, offers particular advantages. The circular-cylindrical circumferential contour U has an imaginary center M. The cylindrical pin 14*a* is disposed away from the center M and to this extent is disposed eccentrically.

In the embodiment shown in FIGS. 1 to 5, the connection portion 9*a* as a female connection portion in the form of the cylindrical bore 13*a* is recessed in the block front side 4*a*. The complementary connection portion 10*a* is correspondingly configured as a male connection portion in the form of the cylindrical pin 14*a* and protrudes axially from the element rear side 7*a*. In a modified embodiment, the arrangement of the female and the male connection portion can be reversed. Accordingly, the reference block can have a preferably removable cylindrical pin, and the compensation element can have a cylindrical bore. Accordingly, the assignment of the male and the female connection portion shown in FIGS. 1 to 5 is not to be considered mandatory.

Further embodiments of surgical instrument systems 1*b*, 1*c*, 1*d* according to the present disclosure are shown in FIGS. 6 to 21. The surgical instrument systems 1*b*, 1*c*, 1*d* in terms of their functionality and design are substantially identical to the surgical instrument system 1*a* according to FIGS. 1 to 5. To avoid repetition, only major differences between the surgical instrument systems 1*b*, 1*c*, 1*d* in relation to the surgical instrument 1*a* according to FIGS. 1 to 5 will therefore be discussed. Functionally identical components and/or portions here are in each case identified with the same reference signs while adding a corresponding suffix.

The surgical instrument system 1*b* differs substantially in that the connection portion 9*b* is a guide slot 15*b* which is incorporated in the block front side 4*a* and is elongate along the anterior-posterior axis AP. The complementary connection portion 10*b* for the different positioning of the compensation element 3*b* engages in this guide slot 15*b* in a form-fitting manner perpendicular to the longitudinal direction of the guide slot 15*b* and so as to be displaceable in the longitudinal direction.

In the embodiment shown, the guide slot 15*b* in portions extends along, more specifically parallel to, the anterior-posterior axis AP. Furthermore, the guide slot 15*b* in portions extends along the medial-lateral axis ML, wherein a parallel orientation is provided in the present case. The guide slot 15*b* in the present case specifically has a longitudinal extent which in the widest sense is hook shaped. Said longitudinal extent is formed by a first longitudinal portion 151*b*, a cross section 152*b*, and a second longitudinal portion 153*b* of the guide slot 15*b*.

Moreover, the guide slot 15*b* in terms of the longitudinal direction thereof is open at one end and to this extent has an introduction opening 154*b*. The introduction opening 154*b* presently is disposed on an upper side, not referred to in more detail, of a circumferential contour UR of the reference block 2*b*. The introduction opening 154*b* is provided for introducing the complementary connection portion 10*b*.

In the embodiment shown, the complementary connection portion 10*b* is a guide pin 16*b*. The guide pin 16*b* is disposed on the element rear side 7*b* and protrudes along the normal direction of the latter. The guide pin 16*b* has a shank portion 161*b* and a head portion 162*b*. The shank portion 161*b* in terms of the diameter thereof, not referred to in more detail, is adapted to a slot width, not referred to in more detail, of the guide slot 15*b*. In the attached state of the compensation element 3*b*, the shank portion 161*b* is held in a form-fitting manner in the guide slot 15*b* perpendicularly to the longitudinal direction of the guide slot 15*b* and in the plane of the block front side 4*b*. The shank portion 161*b* is movable by sliding in the longitudinal direction of the guide slot 15*b*.

Figure 9:
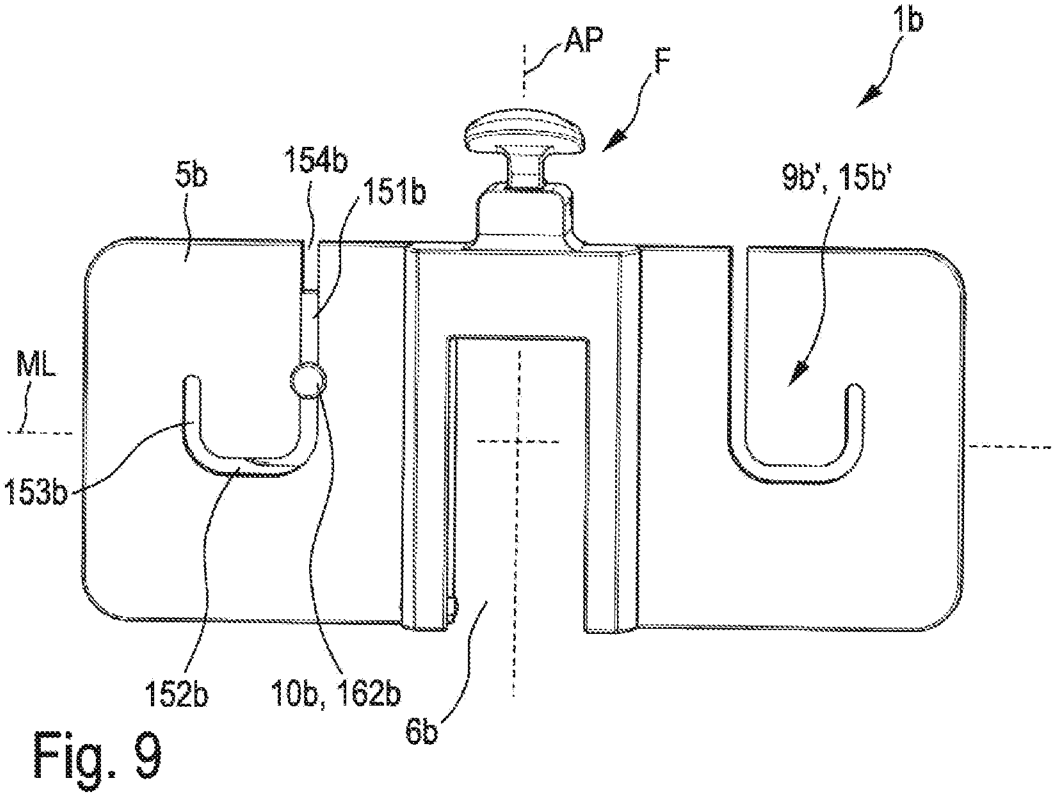
FIG. 9 shows the surgical instrument system according to FIG. 6 in a schematic rear view.
Figure 10:
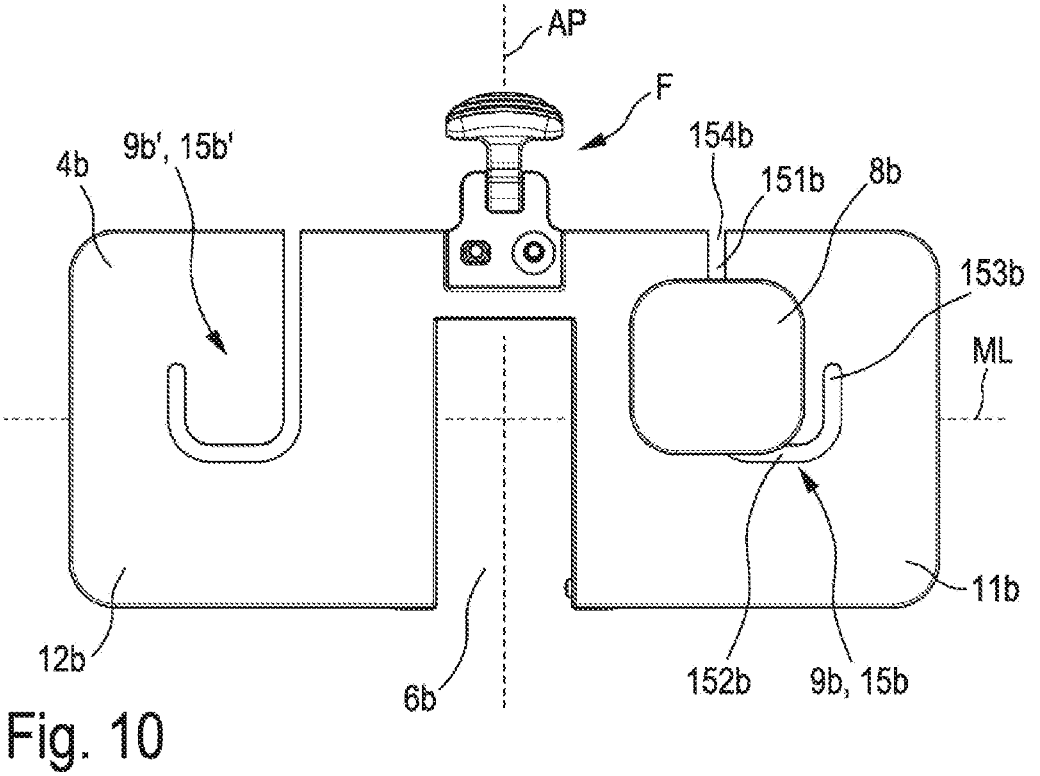
FIG. 10 shows the surgical instrument system according to FIG. 6 in a schematic front view (FIG. 10)
Figure 11:
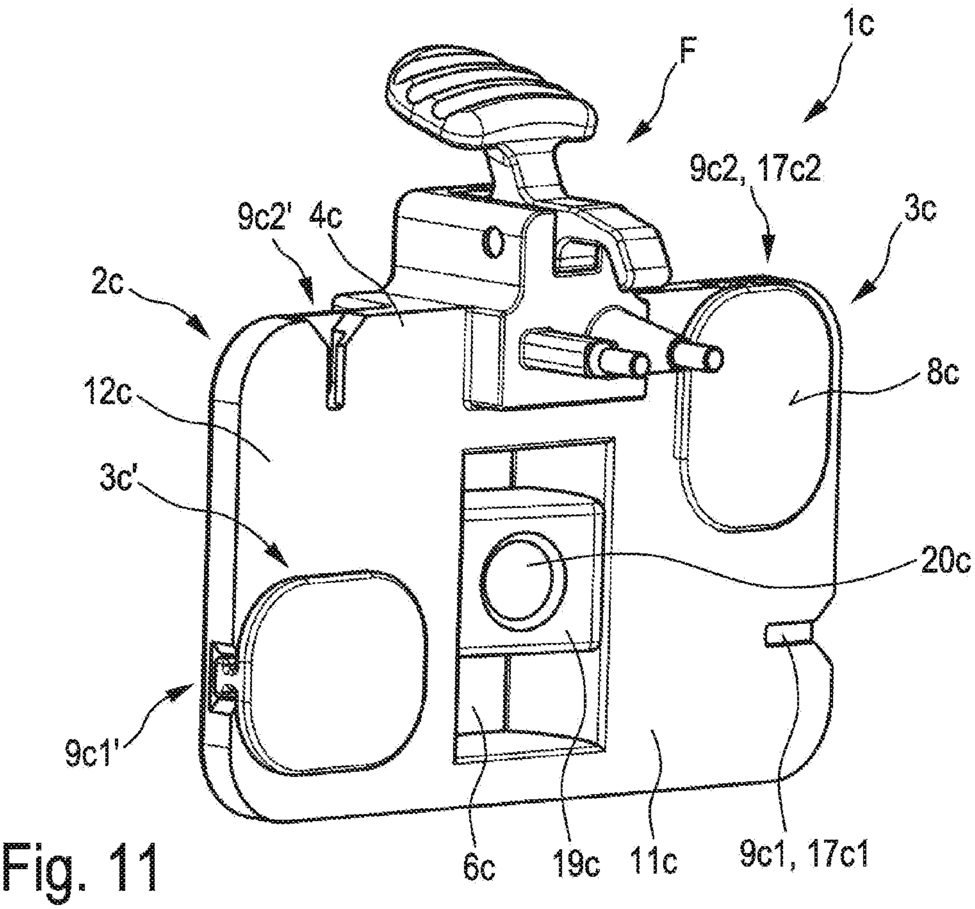
FIG. 11 shows in a schematic perspective view a further embodiment of a surgical instrument system according to the present disclosure.
Figure 12:
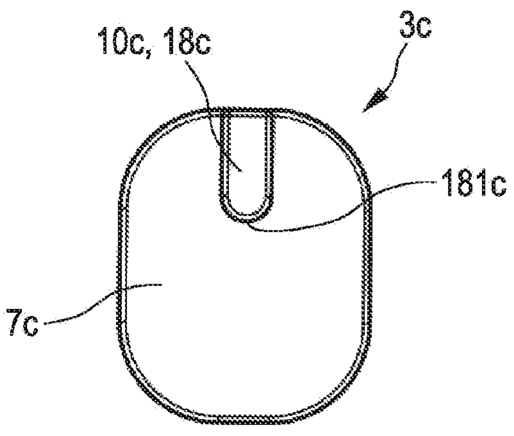
FIG. 12 shows a compensation element of the surgical instrument system according to FIG. 11 in a schematic rear view.
Figure 13:
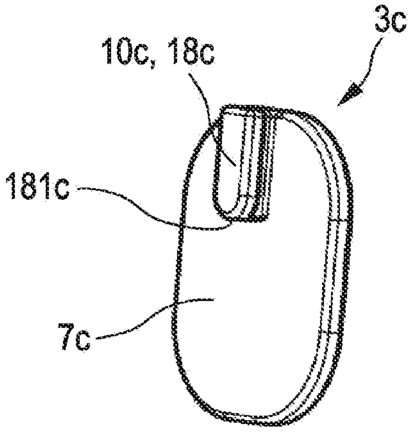
FIG. 13 shows a compensation element of the surgical instrument system according to FIG. 11 in a perspective rear view.
Figure 14:
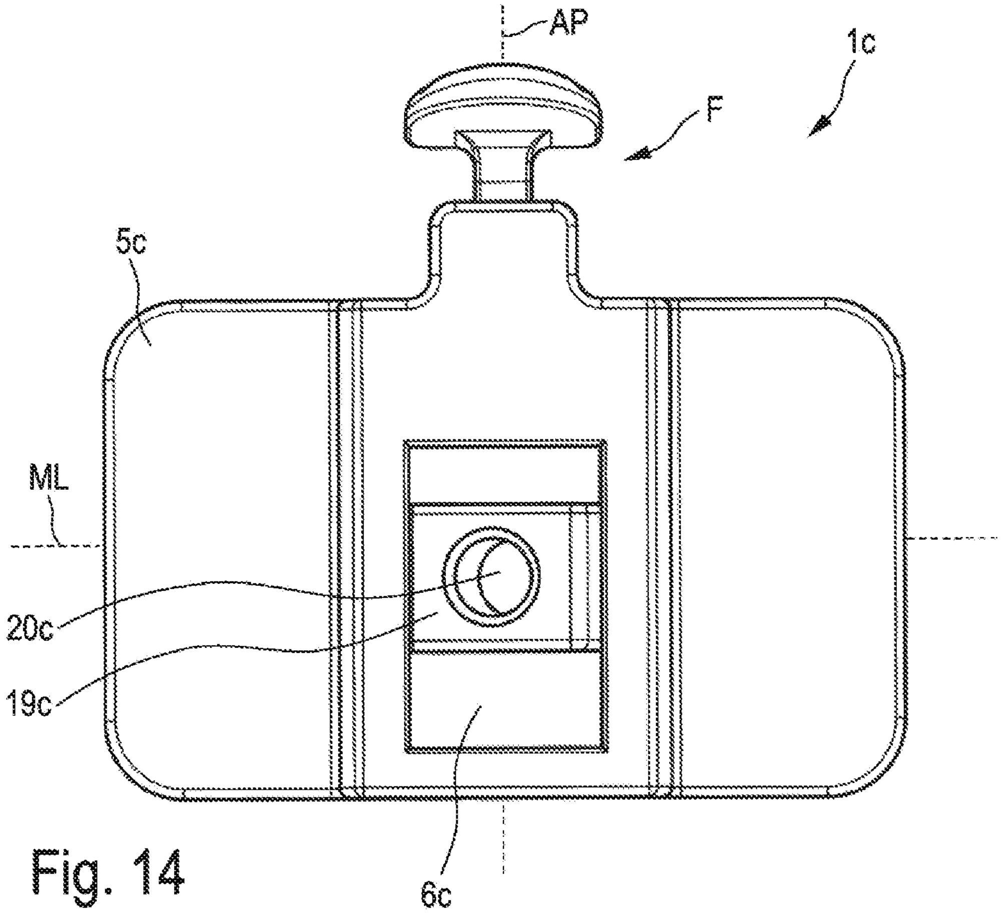
FIG. 14 shows the surgical instrument system according to FIG. 11 in a schematic rear view.
Figure 15:
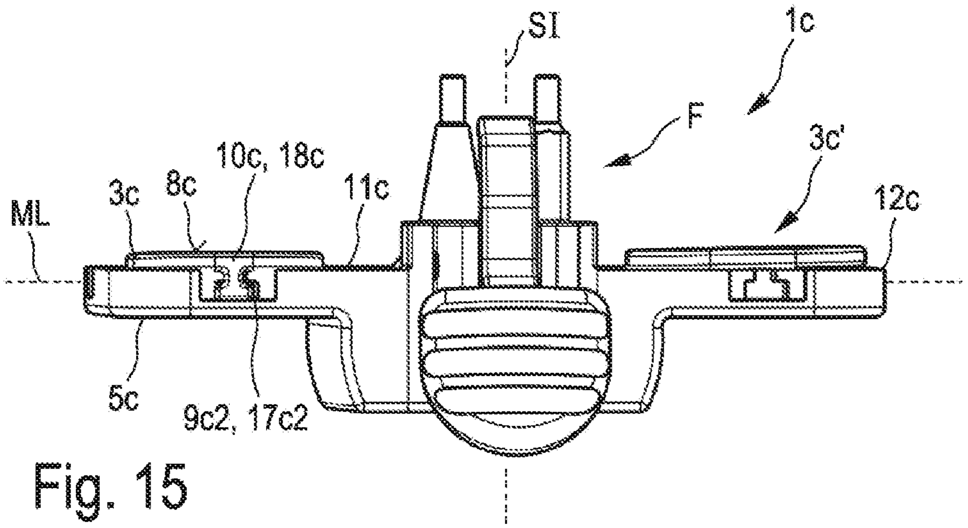
FIG. 15 shows the surgical instrument system according to FIG. 11 in a plan view.
Figure 16:
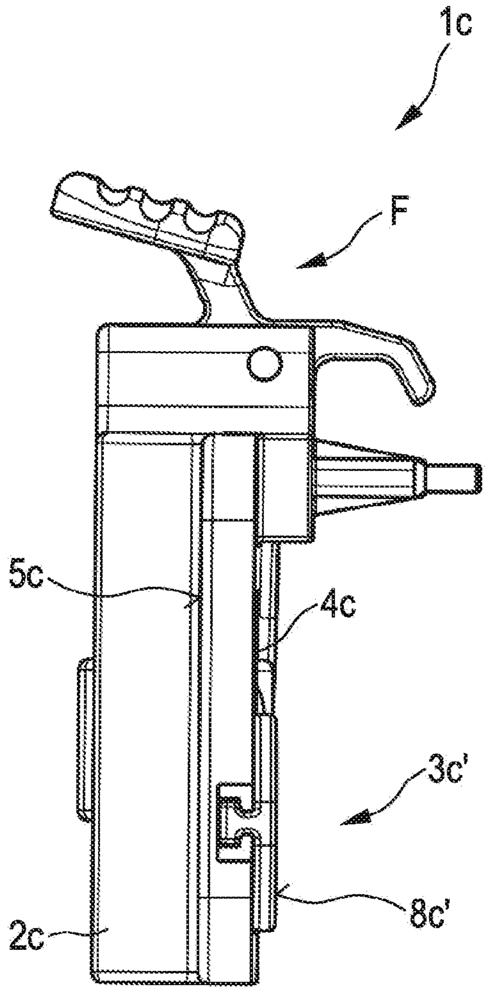
FIG. 16 shows the surgical instrument system according to FIG. 11 in a lateral view.
Figure 17:
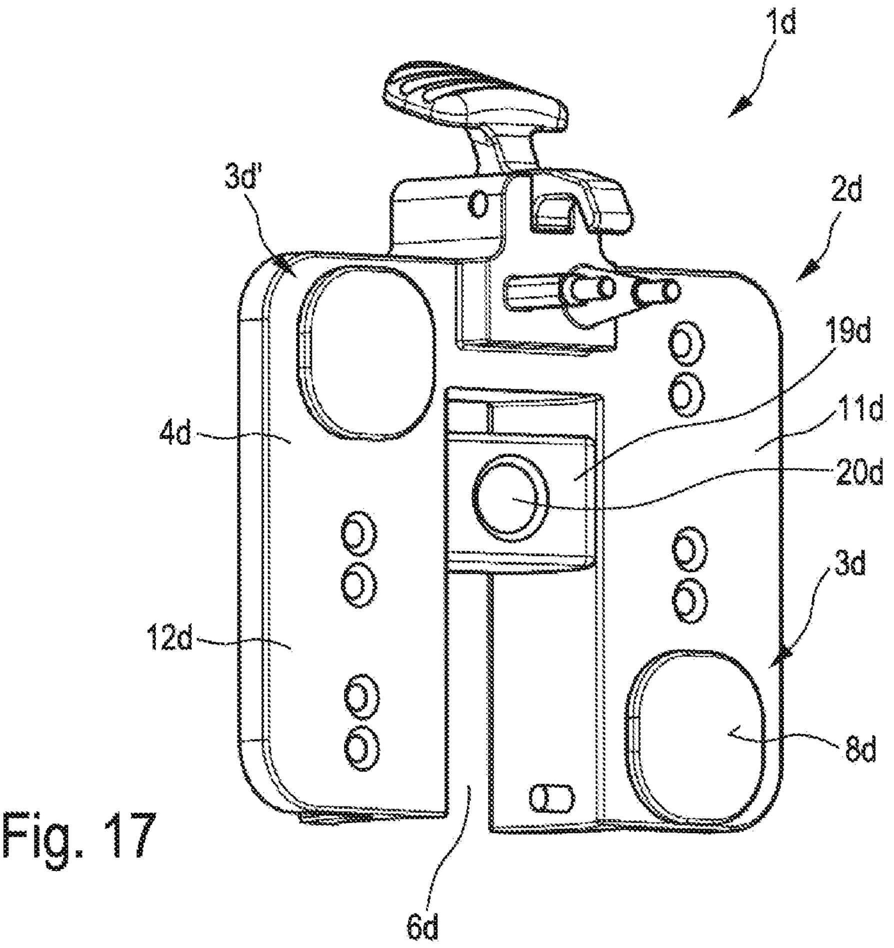
FIG. 17 shows in a schematic perspective view a further embodiment of a surgical instrument system according to the present disclosure.
Figure 18:
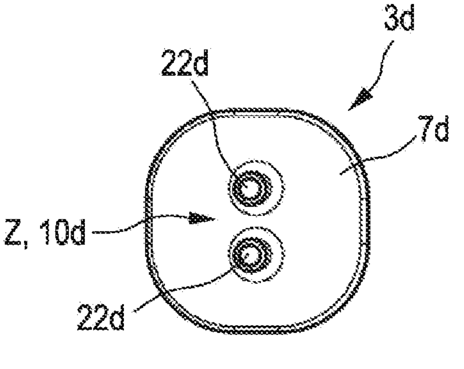
FIG. 18 shows a compensation element of the surgical instrument system according to FIG. 17 in a schematic rear view.
Figure 19:
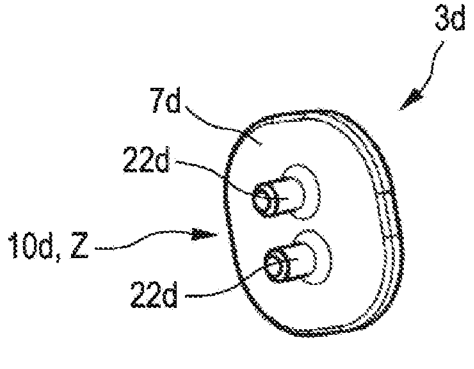
FIG. 19 shows a compensation element of the surgical instrument system according to FIG. 17 in a perspective rear view.
Figure 20:
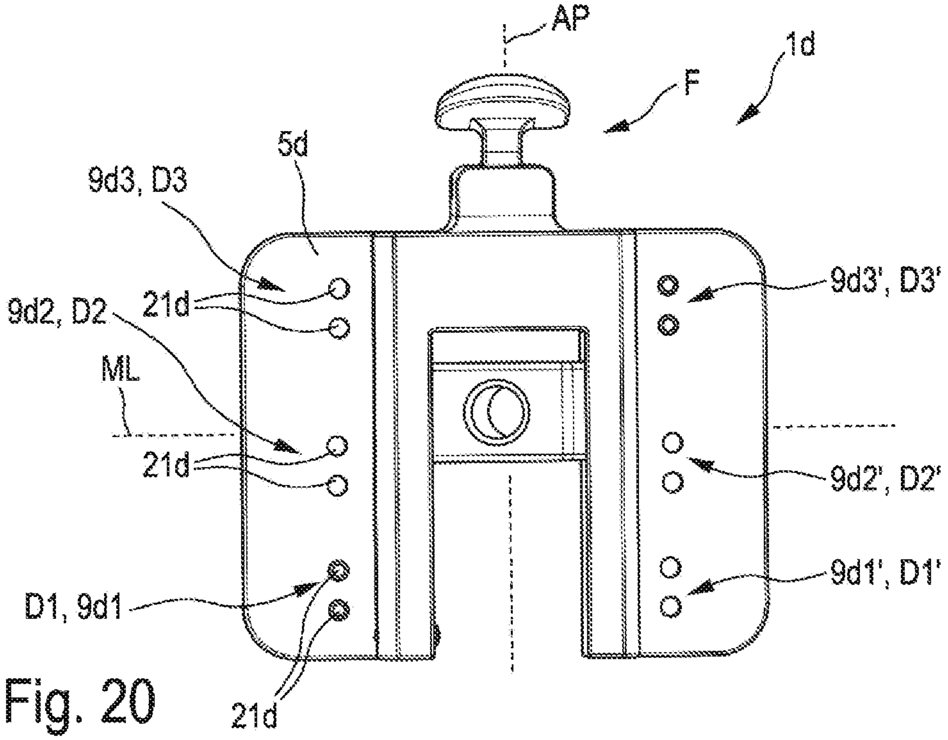
FIG. 20 shows the surgical instrument system according to FIG. 17 in a schematic rear view.
Figure 21:
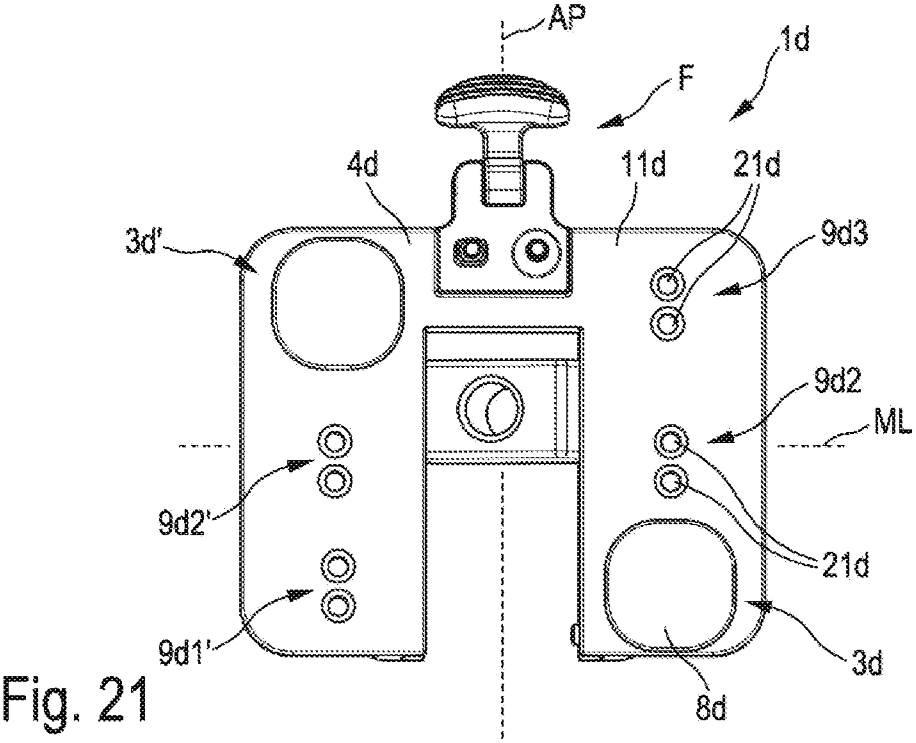
FIG. 21 shows the surgical instrument system according to FIG. 17 in a schematic front view.

The head portion 162*b* is disposed on an end of the shank portion 161*b* that faces away from the element rear side 7*b*. The head portion 162*b* has a larger diameter in comparison to the shank portion 161*b*. The head portion 162*b* serves for captively attaching the compensation element in the normal direction of the block front side 4*b*. In other words, the head portion 162*b* engages behind the block rear side 5*b* such that the compensation element 3*b* cannot be extracted in the normal direction of the block front side 4*b* (FIG. 9).

For attaching the compensation element 3*b* to the reference block 2*b*, the guide pin 16*b* is introduced in the radial direction of the shank portion 161*b* into the introduction opening 154*b*. In the process, the head portion 162*b* in the way described above engages behind the guide slot 15*b*. For positioning the compensation element 3*b*, the shank portion 161*b* is disposed along the longitudinal direction of the guide slot 15*b* and thus within the first longitudinal portion 151*b*, and optionally along the transverse portion 152*b* and/or the second longitudinal portion 153*b*.

The shank portion 161*b* presently has a circular-cylindrical cross section and is accordingly held in the guide slot 15*b* of the reference block 2*b* so as to be rotatable relative to the latter about the longitudinal axis of said shank portion 161*b*, which is not referred to in more detail. As a result, the contact face 8*b* can also be aligned so as to be adapted in a rotary manner, if required.

The guide slot 15*b* in the case of the embodiment shown is incorporated in the medial portion 11*b* of the block front side 4*b* and extends continuously in the depth direction between the block front side 4*b* and the rear side 5*b*.

The connection system of the surgical instrument system 1*b* presently has a further connection portion 9*b*' which is incorporated in the lateral portion 12*b*. The arrangement and/or design of the further connection portion 9*b*' is mirror-symmetrical and otherwise identical to the connection portion 9*b*. Accordingly, the further connection portion 9*b*' is a further guide slot 15*b*'. The compensation element 3*b* can be selectively attached on the medial portion 11*b* or the lateral portion 12*b*.

It is moreover understood that instead of the substantially square circumferential contour of the compensation element 3*b* shown in FIGS. 6 to 10, a circular or otherwise designed circumferential contour may also be provided. To this extent, the square circumferential contour shown is to be understood as purely exemplary. The same applies, mutatis mutandis, to the presently shown, hook-shaped longitudinal extent of the guide slots 15*b*'.

The surgical instrument system 1*c* according to FIGS. 11 to 16 differs substantially from the instrument systems 1*a*, 1*b* in that a plurality of connection portions 9*c*1, 9*c*2 spaced apart along the anterior-posterior axis AP are disposed on the reference block 2*c*. For the different positioning of the compensation element 3*c* the complementary connection portion thereof can be selectively connected to one of the connection portions 9*c*1, 9*c*2 disposed at a spacing.

In the case of the embodiment shown, the medial portion 11*c* as well as the lateral portion 12*c* of the block front side 4*c* have in each case a plurality of connection portions which are correspondingly spaced apart in the vertical direction and can also be referred to as the first medial connection portion 9*c*1, the second medial connection portion 9*c*2, the first lateral connection portion 9_c_1' and the second lateral connection portion 9_c_2'. It is understood that there may be more than the present respective two connection portions, for example three, four, five or even more connection portions, per portion of the block front side 4_c_.

Said connection portions define in each case an attachment point, interface or else connection point for the different positioning of the compensation element. As in the embodiments already explained above, the compensation element 3_c_ is selectively attachable on the medial portion 11_c_ or the lateral portion 12_c_. Aside from the compensation element 3_c_, the configuration shown in FIGS. 11, 15, 16 comprises a further compensation element 3_c_', this to be understood as purely exemplary.

In the present case, the plurality of connection portions 9_c_1, 9_c_2 disposed at a spacing are in each case designed as an undercut groove 17_c_1, or 17_c_2, respectively. The same applies, mutatis mutandis, to the further connection portions 9_c_1', 9_c_2' disposed on the lateral portion 12_c_.

The undercut grooves 17_c_1, 17_c_2 can also be referred to as the first undercut groove 17_c_1 and the second undercut groove 17_c_2. The undercut grooves 17_c_1, 17_c_2 presently differ only in terms of their orientation, wherein the first undercut groove 17_c_1 is elongate parallel to the medial-lateral axis ML. The second undercut groove 17_c_2 is elongate parallel to the anterior-posterior axis AP.

As opposed to the guide slot 15_b_ of the embodiment according to FIGS. 6 to 10, the undercut grooves 17_c_1, 17_c_2 do not extend continuously between the block front side 4 and the block rear side 5_c_. Instead, the undercut grooves 17_c_1, 17_c_2 are incorporated in the block front side 4_c_ without penetrating the block rear side 5_c_. This can be seen in detail in FIGS. 15, 16, for example.

The complementary connection portion 9_c_ of the compensation element 3_c_ is designed as a strip 18_c_. The strip 18_c_ is disposed on the element rear side 7_c_ and protrudes in the normal direction of the latter. The strip 18_c_ has a cross-sectional profile which is not referred to in more detail and corresponds to a cross section of the undercut grooves 17_c_1, 17_c_2. As a result, the compensation element 3_c_ is able to be attached on the block front side so as to be form-fitting in terms of the proximal-distal axis. The strip 18_c_ has a radiused front end portion 181_c_. Said undercut of the grooves 17_c_1, 17_c_2 presently is designed in the shape of a dovetail in the widest sense. The same applies in an analogous manner to the cross section of the strip 18_c_. The grooves 17_c_1, 17_c_2 and the strip 18_c_ form a type of dovetail guide.

For attaching the compensation element 3_c_ to the reference block 2_c_, the strip 18_c_, with the rounded front end portion 181_c_ leading, is pushed into one of the grooves 17_c_1, 17_c_2 on the medial portion 11_c_ or one of the corresponding grooves on the lateral portion 12_c_. This is performed until an end position in which the rounded front end portion 181_c_ impacts an end of the respective groove, not referred to in more detail, is reached. For the different positioning of the compensation element 3_c_, the strip 18_c_ can selectively be pushed into the lower first groove 17_c_1 or the upper second groove 17_c_2.

It is understood that the arrangement of the undercut grooves 17_c_1, 17_c_2 to be seen in FIGS. 11 to 16, as well as the longitudinal orientation thereof, is to be understood as purely exemplary. In an embodiment not shown, in a manner corresponding to the first undercut groove 17_c_1, for example, a plurality of undercut grooves which are elongate parallel to the medial-lateral axis ML are disposed on the medial portion 11_c_ so as to be distributed across the height of the reference block 2_c_. The same can apply, mutatis mutandis, to the lateral portion 12_c_.

Moreover, the reference block 2_c_ has a passage 6_c_ for receiving an intramedullary rod. The passage 6_c_ presently is provided with an insert piece 19_c_. The insert piece 19_c_ has a receptacle bore 20_c_ for directly receiving the intramedullary rod. It is understood that such an insert piece may also be present in the embodiments according to FIGS. 1 to 10.

The compensation element 3_c_ has an approximately rectangular circumferential contour, not referred to in more detail, with rounded corners. This design is understood to be purely exemplary. Instead of the rounded rectangular circumferential contour, a circular circumferential contour as in the embodiment as per FIGS. 1 to 5, or an approximately square circumferential contour as in the embodiment according to FIGS. 6 to 10, may also be provided, for example.

The surgical instrument system 1_d_ shown in FIGS. 17 to 21, so as to correspond to the surgical instrument system 1_c_ according to FIGS. 11 to 16, possesses a plurality of connection portions 9_d_1, 9_d_2, 9_d_3, 9_d_1', 9_d_2', 9_d_3' which are disposed so as to be spaced apart along the anterior-posterior axis AP. Said connection portions 9_d_1, 9_d_2, 9_d_3, 9_d_1', 9_d_2', 9_d_3' are disposed on the medial portion 11_d_ as well as on the lateral portion 12_d_ of the block front side 4_d_. Accordingly, the plurality of connection portions can also be referred to as the first medial connection portion 9_d_1, the second medial connection portion 9_d_2, the third medial connection portion 9_d_3, the first lateral connection portion 9_d_1', the second lateral connection portion 9_d_2', and the third lateral connection portion 9_d_3'.

In embodiments not illustrated in the drawings, fewer or more than the presently shown three connection portions are in each case present on the respective portion of the block front side 4_d_.

Each of the connection portions 9_d_1, 9_d_2, 9_d_3, 9_d_1', 9_d_2', 9_d_3' defines an attachment point and/or connection point. In the configuration shown in FIGS. 17, 20, 21, a compensation element 3_d_ is attached to the first medial connection portion 9_d_1, and a further compensation element 3_d_' is attached to the third lateral connection portion 9_d_3. This again is to be understood as purely exemplary.

The connection portions 9_d_1, 9_d_2, 9_d_3, 9_d_1', 9_d_2', 9_d_3' comprise in each case at least one bore 21_d_ incorporated in the block front side 4_d_. The bores presently are in each case, as a through bore, elongate continuously between the block front side 4_d_ and the block rear side 5_d_ and oriented parallel to the proximal-distal axis SI.

The complementary connection portion 10_d_ of the compensation element 3_d_ correspondingly comprises in each case at least one pin 22_d_ which in terms of dimensions is adapted to the corresponding bores 21_d_. The at least one pin 22_d_ is disposed on the element rear side 7_d_ and protrudes in the normal direction of the latter.

In the embodiment shown, each of said connection portions 9_d_1, 9_d_2, 9_d_3, 9_d_1', 9_d_2', 9_d_3' of the reference block 2_d_ has a plurality of bores 21_d_. More specifically, presently there are exactly two bores 21_d_ per connection portion. Accordingly, the bores form a bore pair. In other words, the connection portions 9_d_1, 9_d_2, 9_d_3, 9_d_1', 9_d_2', 9_d_3' are in each case designed as a bore pair D1, D2, D3, D1', D2' and D3', respectively. The bores of the bore pairs in the embodiment shown are disposed on top of one another in terms of the anterior-posterior axis AP. In embodiments not shown in the figures, a disposal next to one another is alternatively or additionally provided.

The complementary connection portion 10*d*, so as to correspond to the connection portions, is designed as a pin pair Z and consequently has not only one pin but two pins 22*d* disposed adjacently.

In an embodiment not illustrated in the drawings, the connection portions have in each case only a single bore, and the complementary connection portion has only a single pin.

The present design as a bore pair or pin pair, respectively, is particularly robust and moreover counteracts any unintentional rotation of the compensation element in terms of the block front side.

The invention claimed is:

1. A surgical instrument system for use in a total knee arthroplasty, the surgical instrument system comprising:

a reference block which is specified to be attached to a distal femur and has a block front side and a block rear side lying opposite to the block front side along a proximal-distal axis;

at least one compensation element which has an element rear side and a contact face lying opposite the element rear side along the proximal-distal axis, the contact face that is specified to contact at least one of a lateral condyle and a medial condyle of the distal femur; and a connection system which has at least one connection portion that is disposed on the reference block, and at least one complementary connection portion that is disposed on the at least one compensation element, and which connection system is specified to releasably attach the at least one compensation element on the block front side, the at least one compensation element in an attached state does not completely cover the block front side at least in terms of an anterior-posterior axis, and the connection system being configured in such a manner that the at least one compensation element is attachable on the block front side in different positions at least in terms of the anterior-posterior axis by the connection system, wherein the at least one connection portion is a cylindrical bore incorporated in the block front side, and the at least one complementary connection portion is a pin which is disposed eccentrically on the element rear side and in the attached state of the at least one compensation element is inserted axially into the cylindrical bore, wherein the at least one compensation element is positionable in different positions relative to the anterior-posterior axis by means of a rotation about a longitudinal axis of the pin.

2. The surgical instrument system according to claim 1, wherein the at least one connection portion is a female connection portion recessed in the reference block, and the at least one complementary connection portion is a male connection portion protruding from the at least one compensation element.

3. The surgical instrument system according to claim 1, wherein at least one of the contact face and the at least one compensation element has a circular circumferential contour.

* * * * *